United States Patent
Abdullayev et al.

(10) Patent No.: US 11,992,435 B2
(45) Date of Patent: May 28, 2024

(54) NEEDLE INJECTOR AND CARRIER FOR DMEK AND PDEK GRAFTS

(71) Applicant: Lions World Vision Institute, Inc., Tampa, FL (US)

(72) Inventors: Eric Abdullayev, Tarpon Springs, FL (US); Arthur C. Kurz, Safety Harbor, FL (US)

(73) Assignee: LIONS WORLD VISION INSTITUTE, INC., Tampa, FL (US)

( * ) Notice: Subject to any disclaimer, the term of this patent is extended or adjusted under 35 U.S.C. 154(b) by 0 days.

(21) Appl. No.: 16/727,217

(22) Filed: Dec. 26, 2019

(65) Prior Publication Data

US 2020/0206029 A1    Jul. 2, 2020

Related U.S. Application Data

(60) Provisional application No. 62/785,368, filed on Dec. 27, 2018, provisional application No. 62/785,430, filed on Dec. 27, 2018.

(51) Int. Cl.
*A61F 9/00* (2006.01)
*A61F 2/00* (2006.01)
(Continued)

(52) U.S. Cl.
CPC .......... *A61F 9/0017* (2013.01); *A61F 2/0095* (2013.01); *A61F 2/142* (2013.01);
(Continued)

(58) Field of Classification Search
CPC .... A61F 9/0017; A61F 2/0095; A61F 2/1691; A61F 2/142; A61F 2/148;
(Continued)

(56) References Cited

U.S. PATENT DOCUMENTS 5,817,075 A * 10/1998 Giungo .................. A61F 2/148
604/294
8,636,795 B2    1/2014 Torres et al.
(Continued)

FOREIGN PATENT DOCUMENTS

EP    2533724 B1    12/2012

OTHER PUBLICATIONS

Medicel AG (Ch 708083A1) (Nov. 28, 2014). (Year: 2014).*
(Continued)

*Primary Examiner* — Paul B Prebilic
(74) *Attorney, Agent, or Firm* — Shumaker, Loop & Kendrick, LLP; Jeffrey B. Fabian

(57) ABSTRACT

Needle injectors and injector carriers for endothelial keratoplasty are provided. Needle injectors include first, second, and third portions each having a respective conduit therein. A first end of the second conduit is fluidly coupled to a second end of the first conduit, where the second conduit has a maximum diameter greater than a maximum diameter of the first conduit. A first end of the third conduit is configured to be fluidly coupled to a second end of the second conduit, where a second end of the third conduit is configured with a cutting surface for cutting and penetrating eye tissue. Injector carriers include a container, a cap configured to seal an opening of the container, and a coupling means configured to couple the needle injector to the cap and allow the needle injector to be disposed within the container.

14 Claims, 7 Drawing Sheets

(51) Int. Cl.
  *A61F 2/14* (2006.01)
  *A61L 27/36* (2006.01)
  *A61B 17/00* (2006.01)

(52) U.S. Cl.
  CPC .......... *A61F 2/148* (2013.01); *A61L 27/3604* (2013.01); *A61B 2017/00969* (2013.01)

(58) Field of Classification Search
  CPC ...... A61F 2220/0025; A61F 2220/0033; A61F 2230/0008; A61F 2250/0039; A61F 2250/006; A61F 2250/0067; A61F 2250/0068; A61F 2250/0069; A61L 27/3604; A61L 2400/06; A61L 2430/16; A61B 2017/00969; A61B 2560/0418; A61B 2560/0431; A61B 2560/0456; A61B 2560/0443
  See application file for complete search history.

(56) References Cited

U.S. PATENT DOCUMENTS

| | | | |
|---|---|---|---|
| 8,673,002 | B2 | 3/2014 | Walter et al. |
| 2006/0235430 | A1 | 10/2006 | Le et al. |
| 2013/0165860 | A1* | 6/2013 | Doud ................ A61M 39/0247 604/117 |
| 2013/0245554 | A1* | 9/2013 | Inoue .................... A61F 2/148 604/151 |
| 2014/0039456 | A1* | 2/2014 | Lerner ................... A61F 9/007 604/506 |
| 2015/0038893 | A1 | 2/2015 | Haffner et al. |
| 2017/0340428 | A1* | 11/2017 | Szurmann ............... A61F 2/148 |
| 2018/0250224 | A1* | 9/2018 | Yamamoto .............. A61P 27/06 |
| 2018/0333296 | A1* | 11/2018 | Heitzmann .......... A61K 9/0051 |
| 2020/0337825 | A1* | 10/2020 | Perry ..................... A61F 9/007 |
| 2023/0014433 | A1* | 1/2023 | Abdullayev .......... A61F 2/0095 |

OTHER PUBLICATIONS

DMEK EndoGlide specification card taken from https://www.networkmedical.co.uk/ophthalmic/product-type/endoglide/dmek-endoglide on Feb. 27, 2020, 3 pages.
https://corneagen.com/Order-Device/EndoSerter.aspx retrieved on Feb. 27, 2020, 5 pages.
https://www.guntherweiss.com/straiko-modified-jones-tube retrieved on Feb. 27, 2020, 1 page.
https://www.guntherweiss.com/leitr-modified-jones-tube retrieved on Feb. 27, 2020, 1 page.

* cited by examiner

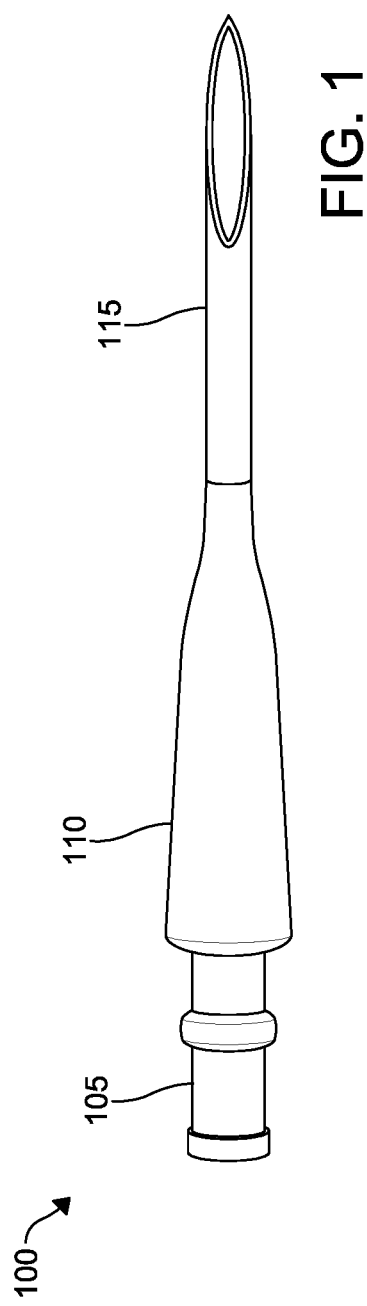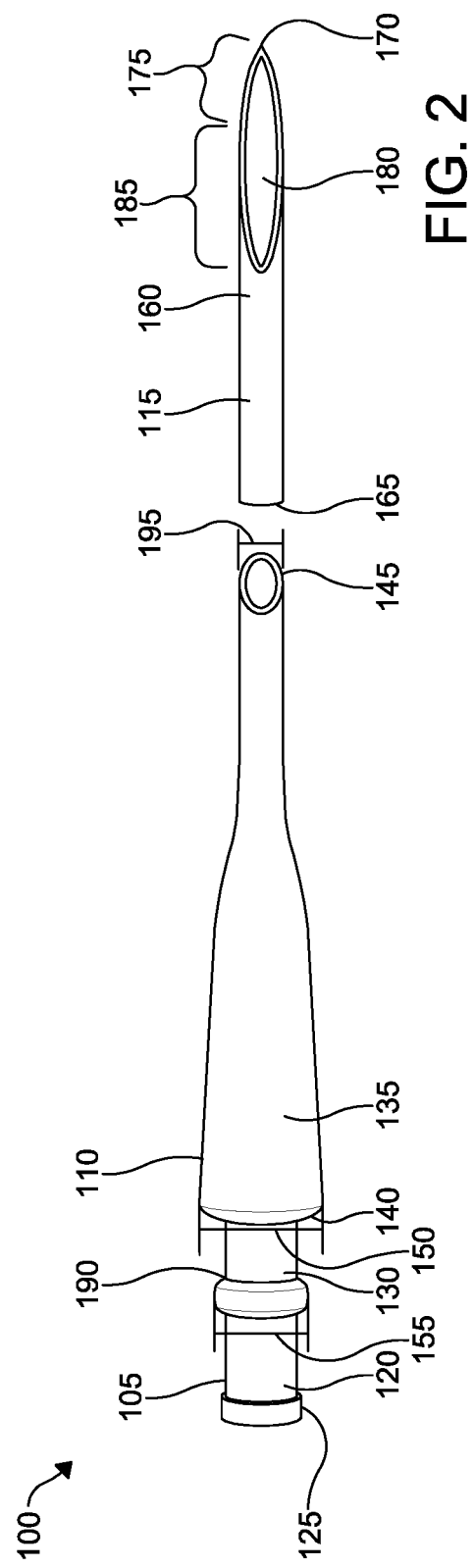

NEEDLE INJECTOR AND CARRIER FOR DMEK AND PDEK GRAFTS

CROSS-REFERENCE TO RELATED APPLICATIONS

This application claims the benefit of U.S. Provisional Application No. 62/785,368, filed on Dec. 27, 2018, and U.S. Provisional Application No. 62/785,430, filed on Dec. 27, 2018. The entire disclosures of the above applications are incorporated herein by reference

FIELD

The present technology relates to a needle injector and carrier for administering ophthalmic tissue into an anterior chamber of an eye, including uses in endothelial keratoplasty including storage, transportation, and transplantation of pre-Descemet's layer and/or Descemet's membrane and endothelium into a recipient's cornea.

INTRODUCTION

This section provides background information related to the present disclosure which is not necessarily prior art.

Corneal transplantation can be dramatically improved using Endothelial Keratoplasty (EK) to include Descemet's Stripping Automated Endothelial Keratoplasty (DSAEK), where an approximately 50-100 micron layer of the Descemet's Membrane (DM) with endothelial cells and cornea stroma can be removed from a donor cornea and transplanted into a patient's/recipient's eye, and Descemet's membrane endothelial keratoplasty (DMEK), where an approximately 7 micron layer of the Descemet's Membrane (DM) with endothelial cells can be removed from a donor cornea and transplanted into a patient/recipient's eye. Pre-Descemet's endothelial keratoplasty (PDEK) is another type of endothelial keratoplasty, where the pre-Descemet's layer (PDL) along with Descemet's membrane (DM) and endothelium is transplanted. However, delivery of such ophthalmic tissue, including the fragile and thin layer of the DM from the donor cornea, can be quite a difficult process, where there is the potential to permanently damage the endothelial cells that are important for restoring healthy vision. DMEK and PDEK procedures require that an incision is made in the patient's eye prior to introduction of the graft into the patient's anterior chamber.

Transplantation of donor ophthalmic tissue into a recipient's eye consequently faces several issues, including aspects related to storage of the ophthalmic tissue, transportation of the ophthalmic tissue, and ultimately the transplantation procedure itself. For example, harvesting donor ophthalmic tissue can occur at various time periods prior to the transplantation procedure. Accordingly, it can be necessary to store the ophthalmic tissue in a medium, such as corneal storage medium, for a time period. It can also be necessary to safely transport the ophthalmic tissue, which can be quite fragile, from a location where the tissue was harvested to another location where the transplantation procedure is to occur. To further facilitate the actual transplantation, an injector or introducer can be preloaded with the ophthalmic tissue, where the injector or introducer is used to insert the ophthalmic tissue into the eye. DSAEK, DMEK and PDEK procedures, for example, can require that an incision be made in the patient's eye prior to introduction of the donor graft into the patient's anterior chamber via the injector or introducer. By providing an injector or introducer preloaded with the ophthalmic tissue, the time investment in the transplantation procedure can be minimized.

Accordingly, there is a need to provide improved ways of carefully, expediently, and successfully storing, transporting, and introducing ophthalmic tissue into an eye, including ways that optimize DSAEK, DMEK, and PDEK procedures and preparation therefor.

SUMMARY

The present technology includes articles of manufacture, systems, and processes that relate to storage, transport, and introducing ophthalmic tissue, including DM and grafts including DM, into a recipient or patient's eye for various restorative procedures, including DSAEK, DMEK, and PDEK.

Certain embodiments include a needle injector for endothelial keratoplasty that includes a first portion, a second portion, and a third portion. The first portion includes a first conduit having a first end and a second end. The second portion includes a second conduit having a first end and a second end, where the first end of the second conduit is fluidly coupled to the second end of the first conduit. The second conduit has a maximum diameter that is greater than a maximum diameter of the first conduit. The third portion includes a third conduit having a first end and a second end, where the first end of the third conduit is configured to be fluidly coupled to the second end of the second conduit. The second end of the third conduit is configured with a cutting surface for cutting and penetrating eye tissue. The first end of the third conduit can be fluidly coupled to the second end of the second conduit; e.g., coupling of the first end of the third conduit to the second end of the second conduit can be reversible.

Certain embodiments include where the needle injector includes an injector carrier. The injector carrier includes a container having an opening, a cap configured to seal the opening of the container, and a coupling means configured to couple the first portion of the needle injector to the cap and allow at least the first portion and the second portion of the needle injector to be disposed within the container when the cap seals the opening of the container. The container can include corneal storage medium and the second conduit can include ophthalmic tissue. The first portion of the needle injector can therefore be coupled to the cap so that at least the first portion and the second portion of the needle injector are disposed within the container so that the ophthalmic tissue contacts the corneal storage medium. In this way, the ophthalmic tissue can be stored and/or transported to a site for performing endothelial keratoplasty.

Certain embodiments include a method for performing endothelial keratoplasty for an eye of a patient. In such a method, a needle injector is provided, as described herein, where the first end of the third conduit is fluidly coupled to the second end of the second conduit and ophthalmic tissue is positioned within the second portion of the needle injector. The second end of the third conduit is inserted into the eye of the patient, where the cutting surface cuts and penetrates the eye of the patient. The ophthalmic tissue is then dispensed from the second conduit of the needle injector through the third conduit of the needle injector into the eye of the patient.

Certain embodiments include a method for performing endothelial keratoplasty for an eye of a patient. In such a method, a needle injector is provided, as described herein, where ophthalmic tissue is positioned within the second portion of the needle injector. An incision is made in the eye of the patient. The second end of the second conduit is inserted through the incision into the eye of the patient. The ophthalmic tissue is then dispensed from the second conduit of the needle injector into the eye of the patient.

Certain embodiments include a method of storing ophthalmic tissue for use in endothelial keratoplasty. A needle injector including an injector carrier is provided, as described herein, where the needle injector is loaded with the ophthalmic tissue. The loaded needle injector is coupled to the cap of the injector carrier. The loaded needle injector is then disposed into the injector carrier, where the ophthalmic tissue contacts corneal storage medium within the container. In this way, the injector carrier including the loaded needle injector can be transported to a site for performing endothelial keratoplasty.

Certain embodiments include various needle injectors used for endothelial keratoplasty that include three portions. A first portion includes a first conduit having a bulb region disposed between a first end and a second end. A second portion includes a second conduit having a first end and a second end, where the first end of the second conduit is fluidly coupled to the second end of the first conduit. The second portion has a first diameter adjacent the first portion that is greater than a diameter of the first portion and the second portion provides a taper toward the second end of the second conduit that ends at a second diameter that is smaller that the first diameter. A third portion includes a third conduit having a first end and a second end, where the first end of the third conduit is fluidly coupled to the second end of the second conduit. The second end of the third conduit is configured with a cutting surface configured for cutting and penetrating eye tissue.

Certain embodiments include various methods for performing endothelial keratoplasty for an eye of a patient. Such methods include providing a needle injector, as described herein, where a graft of ophthalmic tissue is positioned within the second conduit of the needle injector. The second end of the third conduit is inserted into the eye of the patient, where the cutting surface cuts and penetrates eye tissue of the patient. The graft of ophthalmic tissue is then dispensed from the second conduit of the needle injector through the third conduit of the needle injector into the eye of the patient. Alternatively, the third portion of the needle injector can be removed prior to dispensing the graft, where the second end of the second conduit is then inserted thru an incision made in the eye of the patient and the graft of ophthalmic tissue dispensed therefrom.

Certain embodiments include an injector carrier that can be used to carry a needle injector, as described herein, or various other types of injectors or introducers used in endothelial keratoplasty. The injector carrier includes a container having an opening, a cap configured to seal the opening of the container, and a coupling means configured to couple the needle injector, other type of injector, or introducer to the cap. In this way, the needle injector, other type of injector, or introducer can be disposed into the container and the cap can seal the opening of the container. The needle injector, other type of injector, or introducer can include ophthalmic tissue and the container can include corneal storage medium to contact the ophthalmic tissue. For example, where a needle injector as described herein is used in conjunction with the injector carrier, the first portion of the needle injector can be coupled to the cap to allow at least the first portion and the second portion of the needle injector to be disposed within the container when the cap seals the opening of the container.

Certain embodiments include various methods for storing ophthalmic tissue used in an endothelial keratoplasty. Such methods include providing a needle injector and an injector carrier, as described herein, where the ophthalmic tissue is positioned within the needle injector and the needle injector is positioned within the injector carrier. Corneal storage medium is provided within the container of the injector carrier, where the corneal storage medium contacts the ophthalmic tissue when the ophthalmic tissue is positioned within the needle injector.

Certain embodiments include various methods for transporting ophthalmic tissue used in an endothelial keratoplasty. Such methods include obtaining the ophthalmic tissue from a donor. A needle injector and an injector carrier, as described herein, are provided and the ophthalmic tissue is disposed within an needle injector. Corneal storage medium is provided within the container, where the corneal storage medium contacts the ophthalmic tissue when the ophthalmic tissue is positioned within the needle injector and the needle injector is placed within the injector carrier. The injector carrier is then transported to a site for the endothelial keratoplasty.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 shows a first embodiment of a needle injector for introducing DMEK and PDEK grafts into an eye.

FIG. 2 shows a second embodiment of a needle injector for introducing DMEK and PDEK grafts into an eye.

DETAILED DESCRIPTION

Figure 3:
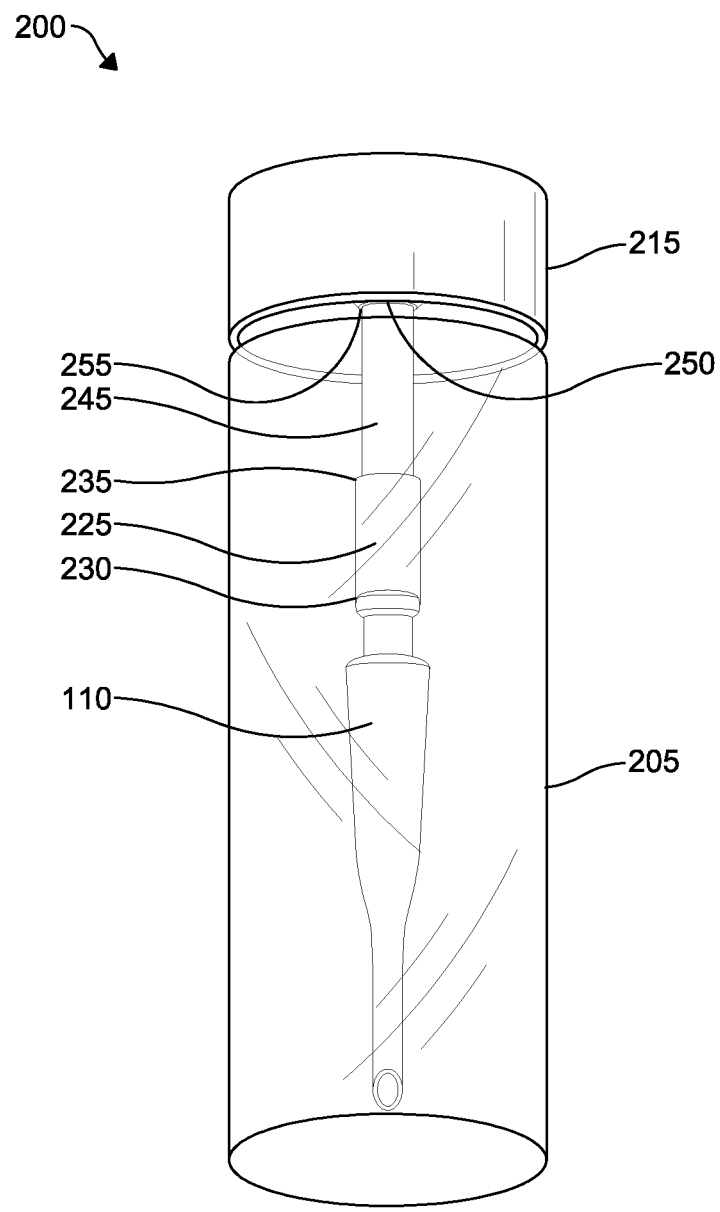
FIG. 3 shows an assembled perspective view of an embodiment of a carrier for a needle injector for introducing DMEK and PDEK grafts into an eye.
Figure 4:
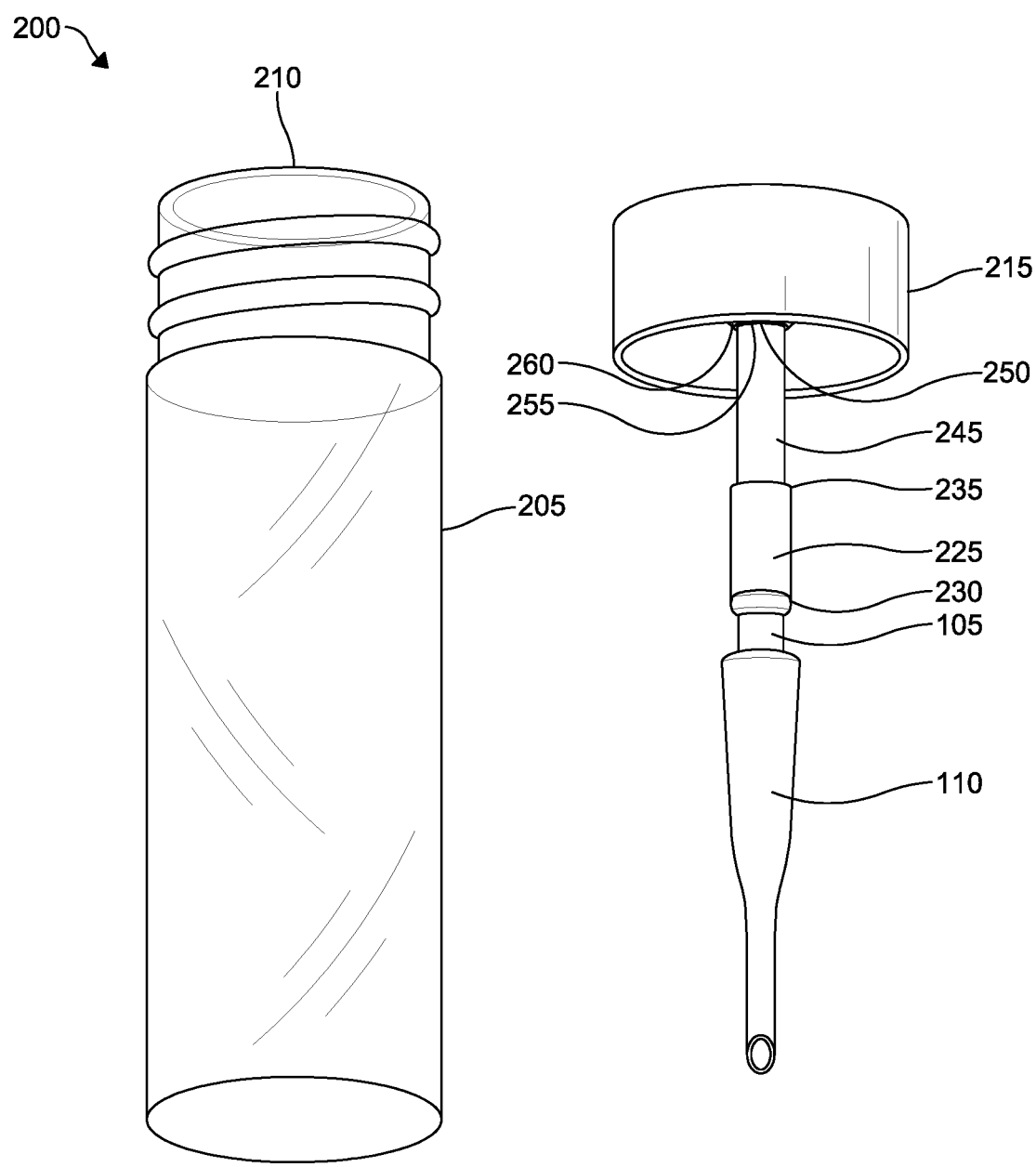
FIG. 4 shows a partially disassembled perspective view of the embodiment of a carrier for a needle injector accordingly to FIG. 3.
Figure 5:
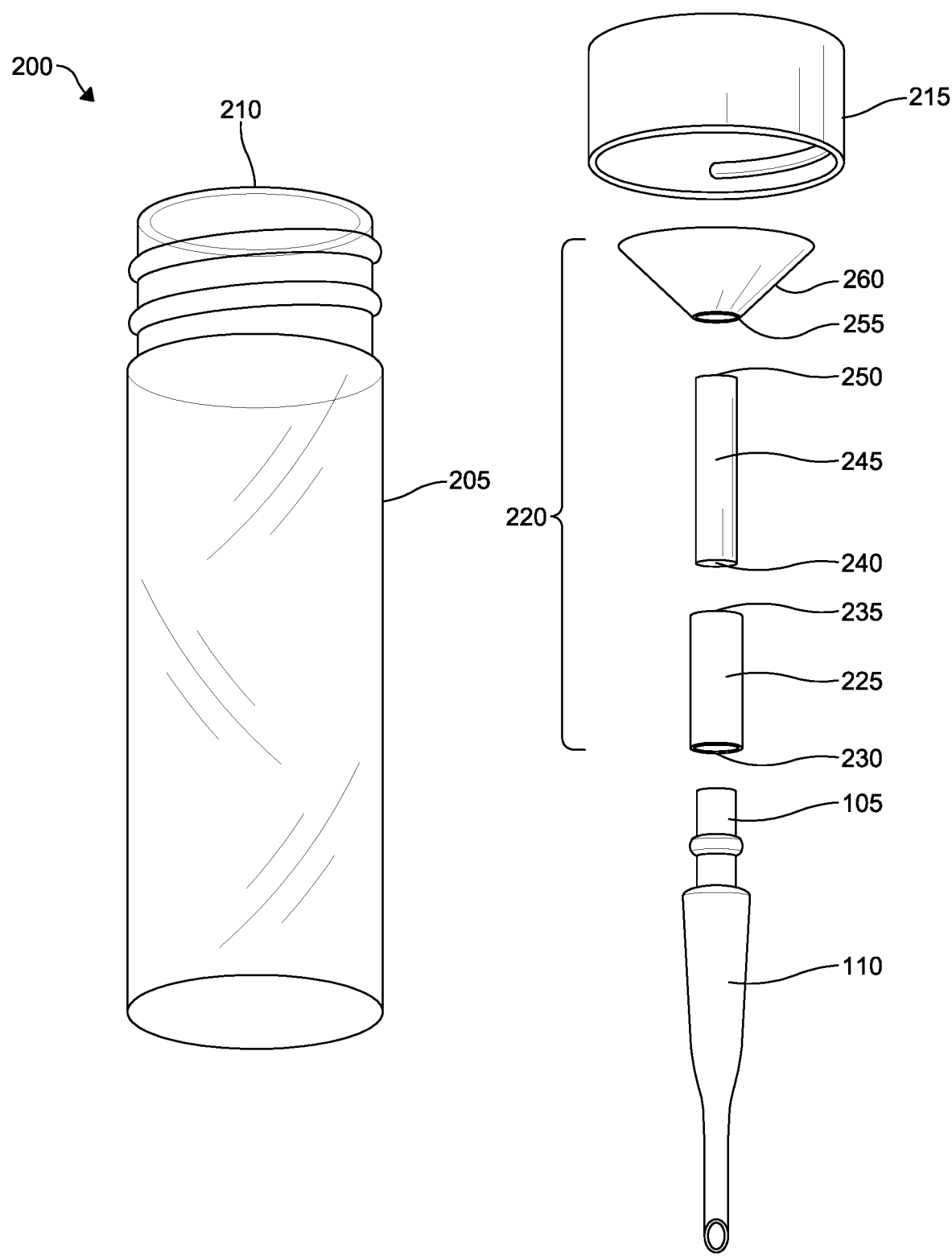
FIG. 5 shows an exploded perspective view of the embodiment of a carrier for a needle injector according to FIG. 3.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The present technology improves administration of ophthalmic tissue into an eye, including uses in endothelial keratoplasty including Descemet's membrane endothelial keratoplasty and Pre-Descemet's endothelial keratoplasty, including where at least a portion of the Descemet's Membrane (DM), which can include endothelial cells, is removed from a donor cornea and transplanted into a patient/recipient's eye. The layer of the DM can be inserted into the front portion (e.g., anterior chamber) of the patient's eye using a particular needle injector or introducer that can cut and penetrate eye tissue of the patient. That is, there is no need to pre-cut or make an incision in the eye prior to use of the needle injector. The graft can then be dispensed from the needle injector into the eye of the patient.

A needle injector for endothelial keratoplasty is provided that has three portions. A first portion includes a first conduit having a first end and a second end. A second portion includes a second conduit having a first end and a second end, the first end of the second conduit fluidly coupled to the second end of the first conduit, and the second conduit having a maximum diameter greater than a maximum diameter of the first conduit. A third portion does not include any openings along its length but does include a third conduit having a first opening at a first end and a second opening at a second end where the first opening and the second opening are the only structures of the third portion through which fluid can pass. The first end of the third conduit is configured to be fluidly coupled to the second end of the second conduit, and the second end of the third conduit configured with a cutting surface for cutting and penetrating eye tissue.

Various embodiments of the needle injector can include the following aspects. The first end of the third conduit can be fluidly coupled to the second end of the second conduit. In this way, the needle injector can be provided preassembled. The first end of the third conduit can be reversibly coupled to the second end of the second conduit so that the needle injector can be used or manipulated without the third portion attached. This affords the user the option of performing an endothelial keratoplasty procedure where an incision is made in the eye and the second end of the second conduit is inserted through the incision to dispense ophthalmic tissue into the eye. Alternatively, the user has the option of having the first end of the third conduit fluidly coupled to the second end of the second conduit, where the second end of the third conduit is inserted into the eye so that the cutting surface cuts and penetrates the eye. The ophthalmic tissue is then dispensed from the second conduit of the needle injector through the third conduit of the needle injector into the eye of the patient.

Various embodiments of the needle injector can include the following additional aspects. The first conduit and the second conduit can be comprised by a single piece of glass. The cutting surface of the second end of the third conduit can be comprised by metal. For example, the third conduit can be a hollow metal tube having a beveled end similar to a hypodermic needle. The cutting surface can be located at a distal end of an opening at the second end of the third conduit and a remainder of the opening can have a non-cutting surface. The cutting surface can be configured as a lancet style blade where a remainder of the bevel opening can have a non-cutting surface. The first conduit can have a bulb disposed between the first end and the second end thereof. The bulb can be used to engage or define coupling with other components as described herein. The bulb can also be used to engage or define coupling with fluid manipulation devices, such as a syringe having a barrel and plunger.

Various embodiments of the needle injector can further include the following aspects. The second conduit can include a chamber which results in the maximum diameter of the second conduit being greater than the maximum diameter of the first conduit. The chamber can be sized and shaped to accommodate, store, and dispense a graft of ophthalmic tissue for endothelial keratoplasty. For example, the ophthalmic tissue can be loaded into the needle injector through the first conduit and stored within the chamber of the second conduit. At least a portion of the second conduit can taper in a direction from the first end of the second conduit towards the second end of the second conduit. Where the second conduit includes the chamber, the chamber can be tapered in this fashion. The taper can facilitate dispensing the ophthalmic tissue from the second conduit into the eye. The second end of the second conduit can have a diameter that is less than the maximum diameter of the first conduit. In this way, it can be easier to load the ophthalmic tissue into the needle injector through the larger maximum diameter of the first conduit, while the smaller diameter of the second end of the second conduit minimizes the size of the portion of the needle injector that is introduced into the eye. The second end of the second conduit can also be configured to fit into the first end of the third conduit. In this way, the ophthalmic tissue does not have to conform to a smaller diameter or overcome a lip or edge in the transition between the second conduit and the third conduit.

Various embodiments of the needle injector can include the following aspects. The first conduit can be about 0.8 cm to about 0.9 cm in length and can provide entry for loading the prepared ophthalmic tissue/graft (e.g., DMEK graft) and can be configured for connection to a syringe. Where the first conduit includes the bulb, the bulb can provide a tighter connection with a coupling means of an injector carrier. The second conduit can be about 1.9 cm to about 2.0 cm in length and can have a diameter to provide adequate corneal storage media irrigation to ophthalmic tissue contained therein. For example, where the second conduit includes a chamber or a tapered chamber, the chamber can provide a volume optimized for contact between the ophthalmic tissue and cornel storage medium; e.g., where the ophthalmic tissue is not folded or constrained so corneal storage medium cannot contact a part thereof. The ophthalmic tissue can be positioned in the second conduit during transportation/storage. The third conduit can be about 1.9 cm to about 2.0 cm in length and can provide the exit for the ophthalmic tissue. The second end of the third conduit can be inserted by puncture into a recipient's anterior chamber where the graft is then unloaded. The total length of the needle injector can be about 4.5 cm to about 4.8 cm.

One end of the needle injector can be configured with a cutting surface for cutting and penetrating eye tissue. For example, the one end of the needle injector can be configured like a portion of a hypodermic needle having a hollow portion or conduit ending in a sharp point intended to puncture through outer eye tissue; e.g., cutting through the cornea to enter the anterior chamber of the eye. The cutting surface can be located at the second end of the third portion of the needle injector, where the cutting surface can include a beveled edge of a length and shape that can be tailored to optimize cutting dependent on bore size. The cutting surface can be formed of a material that can be sharpened or manufactured with a sharp edge configured for cutting through the outer surface of the eye allowing the needle injector to penetrate into the interior of the eye. For example, the third portion of the needle injector can be configured much in the same fashion as the end of a beveled hypodermic needle, where a leading portion at the distal end of the beveled opening can form a cutting surface or lancet and the trailing portion of the beveled opening can form a non-cutting surface. In this way, the amount of the eye and subsequent wound profile is minimized, where the remainder of the beveled opening can push through the cut without having to increase the size of the cut.

The needle injector can manufactured and assembled in various ways. In some embodiments, the needle injector can be formed as a single integrated unit including all three portions connected to each other as one piece, where no assembly is necessary prior to use. In other embodiments, the needle injector can initially include two separate parts—a first part including the first and second portions and a second part including the third portion. The first part can be formed of a single piece of glass that embodies the first portion and the second portion. The second part can be formed of a single piece of metal that embodies the third portion. For full assembly of the needle injector, the first and second parts can be coupled by disposing the second end of the second conduit into the first end of the third conduit.

Coupling can be reversible or can be made essentially permanent by press-fitting or through use of an adhesive, for example.

Alternatively, the third portion of the needle injector can be detachable during use of the needle injector. This provides the user the option of using the needle injector with the third portion to cut through the outer surface of the eye to allow the needle injector to penetrate into the interior of the eye and dispense ophthalmic tissue therefrom, or the option of using the needle injector by detaching and removing the third portion, where the second end of the second portion of the needle injector can be inserted through a pre-cut incision in the eye and the ophthalmic tissue dispensed therefrom. For example, the second end of the second portion of the needle injector can be dimensioned to fit into an incision used in prior endothelial keratoplasty methods.

The needle injector can be provided or used in conjunction with an injector carrier. The injector carrier can include a container, a cap, and a coupling means. The container has an opening and the cap is configured to seal the opening of the container. The coupling means is configured to couple the first portion of the needle injector to the cap and allow at least the first portion and the second portion of the needle injector to be disposed within the container when the cap seals the opening of the container. In this way, the injector carrier can be used to transport and protect the needle injector, including where the needle injector holds ophthalmic tissue in contact with corneal storage medium within the container. The container of the injector carrier can be sized to accommodate the needle injector where the first and second portions are separated from the third portion. The container of the injector carrier can also be sized to accommodate the needle injector where first and second portions are coupled to the third portion; e.g., where the first end of the third conduit is fluidly coupled to the second end of the second conduit. In any instance, the injector carrier can be configured to hold the needle injector within the container without contacting an interior wall or bottom of the container.

Various embodiments of the injector carrier can include the following aspects. The coupling means can include a resilient member having a first end configured to fit over the first end of the first conduit. The resilient member can also have a second end that fits over a first end of a stem coupled to the cap. A second end of the stem can be fit into an opening within a sealing member coupled to the cap, where the sealing member is configured to seal the opening of the container. For example, the resilient member can be configured as a short piece of plastic tubing or collar serving to couple the needle injector (e.g., the first end of the first conduit) to the stem depending from the sealing member and cap. The container of the injector carrier can include corneal storage medium, including an amount of corneal storage medium sufficient to contact ophthalmic tissue in the needle injector when at least the first portion and the second portion of the needle injector are disposed within the container when the cap seals the opening of the container.

Methods for performing endothelial keratoplasty for an eye of a patient are provided that can employ a needle injector and/or an injector carrier as described herein. A needle injector, as described herein, can be provided where the first end of the third conduit is fluidly coupled to the second end of the second conduit and ophthalmic tissue is positioned within the second portion of the needle injector. The second end of the third conduit can be inserted into the eye of the patient, where the cutting surface cuts and penetrates the eye of the patient. The ophthalmic tissue can then be dispensed from the second conduit of the needle injector through the third conduit of the needle injector into the eye of the patient.

Other methods for performing endothelial keratoplasty for an eye of a patient are provided that can employ a needle injector and/or an injector carrier as described herein. A needle injector, as described herein, can be provided where ophthalmic tissue is positioned within the second portion of the needle injector. An incision can be made in the eye of the patient. The second end of the second conduit can be inserted through the incision into the eye of the patient. The ophthalmic tissue can then be dispensed from the second conduit of the needle injector into the eye of the patient.

Methods of storing ophthalmic tissue for use in endothelial keratoplasty are provided that can employ a needle injector as described herein and an injector carrier as described herein. The needle injector can be loaded with the ophthalmic tissue. The loaded needle injector can be coupled to the cap of the injector carrier. The loaded needle injector can then be disposed into the injector carrier, where the ophthalmic tissue contacts corneal storage medium within the container. It should be noted that such methods can also be practiced using injectors or introducers for endothelial keratoplasty other than the needle injector described herein, where the injector carrier as described herein is configured to accommodate the other injector or introducer. Such methods can further include transporting the injector carrier including the loaded needle injector to a site for performing endothelial keratoplasty.

In certain embodiments, the present technology provides various methods of using the needle injector. These include ways of loading a graft or ophthalmic tissue into the injector, ways of assembling the injector, and ways of administering the graft or ophthalmic tissue; e.g., performing keratoplasty. The following exemplary methods include a series of steps where it will be evident to one skilled in the art that the order of certain steps can be different in various embodiments while the order of other certain steps cannot be changed relative to each other. Similarly, additional steps can be included in the various embodiments of the present technology and certain steps may be omitted in certain embodiments of the present technology.

The present technology further includes various injector carriers that can be preloaded with ophthalmic tissue and that contain corneal storage medium, where such injector carriers can be used for storage, transport, and transplantation purposes. Various facets from the collection of donor tissue through to the administration of the ophthalmic tissue into a recipient's eye can be improved thereby. For example, benefits are realized for Descemet's membrane endothelial keratoplasty and Pre-Descemet's endothelial keratoplasty, where at least a portion of the Descemet's Membrane (DM), which can include endothelial cells, is removed from a donor cornea and transplanted into a recipient's eye. The layer of the DM can be inserted into the front portion (e.g., anterior chamber) of the recipient's eye using a particular injector or introducer. The present injector carrier can be configured to accommodate various injectors or introducers, including the needle injectors described herein, which are preloaded with endothelial tissue grafts, allowing safe and secure storage and transportation of the ophthalmic tissue while in contact with corneal storage medium; e.g., Optisol-GS corneal storage medium. The injector carrier allows easy removal of the injector from the corneal storage medium for use in endothelial keratoplasty.

Embodiments of an injector carrier for ophthalmic tissue used in an endothelial keratoplasty can include a container and a lid configured to seal the container. The injector carrier can also include an injector and a coupling device. The injector can include a conduit fluidly coupling a first end to a second end, where the conduit includes a portion configured to accommodate the ophthalmic tissue for the endothelial keratoplasty. The coupling device is configured to couple one of the first end and the second end of the injector to an interior face of the lid. In this way, the injector depends or projects from the interior face of the lid. Removal of the lid from the container allows easy removal of the injector, including any ophthalmic tissue loaded into the injector. Corneal storage medium can be provided that contacts the ophthalmic tissue when the ophthalmic tissue is positioned within the injector.

In certain embodiments, the injector carrier can include a sealing means in the form of a cone that is coupled to the interior face of a cap for a container. The container can take the form of vial having a length greater than a diameter thereof. A stem can act as an intermediate coupling between the cone and a piece of tubing or collar, where the stem can have a first end coupled to the cone and a second end coupled to a first end of the tube. A second end of the tube can receive one of the first end and the second end of the injector. The tubing or collar can be configured to receive one end of the injector and can be tailored to work with various types, shapes, and configurations of injectors or introducers, including the needle injectors described herein. For example, the tubing can be resilient and flexible and can slip over an end of the injector, where depending on the flexible nature, the tubing can stretch and flex to accommodate injectors having different sized ends. Alternatively, the tubing of the injector carrier can be replaced with a different sized tubing to accommodated a different sized injector end. In other embodiments, the tubing can be deleted and the stem can be configured to be disposed within an end of the injector. The stem can be compressible in such instances. The stem can be configured as a solid stem or plastic stick that can be coupled or directly connected securely at an end thereof to the cone on the interior face or inner surface of the cap. The stem can also be a portion of a handle from an ocular sponge used in preparing the ophthalmic tissue graft.

In certain embodiments, the injector can be made of glass and can connect vertically to the bottom of the stem using the tubing, where the injector can be disposed within the container (e.g., a glass vial) in a vertical position with minimal handling and movement of the injector. To remove the injector from the container, for example, the cap can be a screw cap that needs to be unscrewed, where the cap can be lifted upwards to remove the injector from the container. The injector can then be detached from the stem, keeping the tubing connected to the injector, where the tubing can then be connected to a syringe or other device for dispensing the ophthalmic tissue from the injector; e.g., as part of an endothelial keratoplasty procedure.

The injector carrier can also be used in various methods of storing ophthalmic tissue. Such methods can include where an injector carrier is provided and ophthalmic tissue is positioned within an injector. Corneal storage medium is provided within the container of the injector carrier, where the corneal storage medium contacts the ophthalmic tissue when the injector is disposed within the injector carrier. In this way, the injector carrier can maintain viability of the ophthalmic tissue during storage and/or transport.

The injector carrier can also be used in various methods of transporting ophthalmic tissue. Such methods can include where the ophthalmic tissue is obtained from a donor. An injector carrier as described herein is provided and the ophthalmic tissue is disposed within the injector. Corneal storage medium is provided within the container, where the corneal storage medium contacts the ophthalmic tissue when the ophthalmic tissue is positioned within the injector. The injector carrier, including the injector with the ophthalmic tissue disposed therein, is then transported to a site for the endothelial keratoplasty, for example.

In certain embodiments, the present technology provides various methods of using the injector carrier. These include ways of loading a graft of ophthalmic tissue into the injector, ways of assembling the injector carrier, and ways of administering the graft or ophthalmic tissue using the injector carrier; e.g., performing keratoplasty. The following exemplary methods include a series of steps where it will be evident to one skilled in the art that the order of certain steps can be different in various embodiments while the order of other certain steps cannot be changed relative to each other. Similarly, additional steps can be included in the various embodiments of the present technology and certain steps may be omitted in certain embodiments of the present technology.

Various embodiments of a needle injector and an injector carrier can be used as follows to load ophthalmic tissue (e.g., a prepared graft) as follows.

Loading a Prepared Graft
1. Use universal scissors to cut a small (approximate ½ inch) piece of suction tubing to fit the injector.
2. Connect one side of the suction tubing to a narrow end of the injector and the other side to a 1 cc syringe.
3. Depress the plunger of the syringe to transfer media to the injector from the syringe, ensuring no air bubbles are present.
4. Place a wide end of the injector next to the prepared graft of ophthalmic tissue and use suction from the syringe to move the graft into the injector, until the graft is in a wide central portion of the injector.
5. Gently disconnect the syringe from the tubing at the narrow end of injector, making sure that the wide end of the injector stays in the corneal storage medium during disconnection.
6. Reconnect syringe to the tubing at the wide end of injector, making sure that the narrow end of the injector remains submerged in the medium.
7. Plug the narrow end of the injector with a thin (e.g., 1 mm wide) piece of wet eye spear for security; injector is ready for transportation.
8. Couple the tubing to the stem and cone of the coupling device of the injector carrier and place injector in an upright position (narrow end down) into the container (e.g., vial) of the injector carrier, where the container includes corneal storage media.

Various embodiments of the injector carrier can be used (e.g., in an operating room) for administration of the ophthalmic tissue (e.g., a prepared graft) as loaded into the injector as follows.

Assemble Injector in Operating Room
1. Prepare basin with an intraocular irrigating solution (e.g., balanced salt solution (BSS)) enough to submerge 3 cc syringe and injector.
2. Gently remove injector (containing ophthalmic tissue) from the container of corneal storage media by removing the lid from the container and lifting the lid with attached coupling device (e.g., cone, stem, tubing) and injector.
3. Place the injector into the prepared basin with BSS, decouple the tubing from the stem, leaving the tubing attached to the injector in the basin, making sure the injector is submerged and no air bubbles observed inside the injector.
4. As submerged, slowly connect the tubing attached at the wide end of the injector to a 3 cc syringe with BSS and leave it in basin with BSS.
5. As submerged, gently place the narrow end of the injector against the wall of the basin, so the plug touches that wall. Very slowly depress the plunger of the syringe to transfer BSS from the syringe to the injector, ensuring there are no air bubbles present. Corneal storage medium will start exiting injector through the narrow end and plug and BSS will replace corneal storage medium inside of the injector.
6. Leave prepared syringe with connected injector in the basin.
7. Prepare recipient/patient.
8. As submerged, remove plug from the narrow end of the injector.
9. Remove the prepared syringe from the basin with connected injector by holding syringe body and transfer onto operating field.
10. Place narrow end of the injector next to the periphery of the patient's cornea.
11. By pushing on the syringe body, insert end of injector into the anterior chamber of the recipient, make sure the end is completely visible in the chamber.
12. Gently depress the plunger of the syringe to transfer prepared ophthalmic tissue graft from the injector into the anterior chamber of the recipient, ensuring there are no air bubbles present.
13. Confirm the presence of the graft in the cavity of the anterior chamber and gently remove narrow end of the injector from the anterior chamber.
14. Perform appropriate steps to unfold donor ophthalmic tissue graft within recipient's eye.

Various benefits and advantages are obtained by the design and use of the needle injector provided by the present technology. These include the ability of the needle injector to enter into the eye through the small needle-like puncture, which results in a smaller wound to the eye versus other methods of making an incision in the eye. In particular, use of the present needle injector does not require a prior blade (e.g., keratome) incision to be entered into eye. This can preserve integrity of the eye and has the potential to decrease astigmatism in the patient receiving the graft. The needle injector also has the advantage that the needle injector can flexibly include various configurations of the first and second portions thereof along with various types of the third portion thereof. For example, one or more third portions can be provided with the needle injector, where the third portions can have various dimensions, bore sizes, bevels, cutting surfaces, etc., where a particular third portion can be selected based on the patient's eye geometry and/or where and how the ophthalmic tissue is to be dispensed. The needle injectors described herein can also be dimensioned to fit within various injector carriers, including various storage/transport containers for holding, storing, and transporting ophthalmic tissue pre-loaded into the needle injector with or without the third portion of the needle injector coupled to the remainder of the needle injector. For example, the needle injector can be secured in an injector carrier or container or vial along with Optisol-GS corneal storage medium, the needle injector removed therefrom at a site for performing endothelial keratoplasty, the first end of the third conduit fluidly coupled to the second end of the second conduit, the second end of the third conduit inserted into the eye of the patient so that the cutting surface cuts and penetrates the eye of the patient, and the ophthalmic tissue dispensed from the second conduit of the needle injector through the third conduit of the needle injector into the eye of the patient.

Various benefits and advantages are obtained by the design and use of the injector carrier provided by the present technology. In particular, the coupling device of the injector carrier can be configured for coupling with various types of injectors. Where the coupling device includes the tubing, for example, the flexible nature of the tubing can allow various dimensions of injector ends to be disposed therein. Alternatively, an end of the tubing could be compressed and inserted into an end of an injector or the tubing can be eliminated and the stem configured to fit within an end of the injector. The injector carrier can also be provided with multiple coupling devices, including one or more cones of various dimensions, one or more stems of various dimensions, and/or one or more tubings of various dimensions to provide a universal set of coupling devices so that the injector carrier can accommodate various dimensioned injectors or introducers, including the needle injectors described herein. For example, the coupling device of the injector carrier can be configured to couple injectors such as the Striko modified Jones tube and LEITR MICRO modified Jones tube for DMEK/PDEK 2.0 incision.

The injector carrier also reduces the steps and components required for preparation and introduction of donor ophthalmic tissue, as where the tubing of the injector carrier can also function as a suction tube for loading the injector with the ophthalmic tissue and as a coupling interface with a syringe for dispensing the ophthalmic tissue from the injector. The stem can also be derived from the handle of an ocular sponge used during preparation of the ophthalmic tissue graft. The injector carrier also minimizes the chance that the ophthalmic tissue will stick to an inner surface of the injector, where the injector carrier allows vertical positioning of the ophthalmic tissue during storage and/or transportation. The injector carrier further improves removal of the injector from the container (e.g., storage/transport vial), where the coupling of the injector to the inner surface of the lid allows simple removal of the lid from the container and withdrawal of the injector from the container using the lid (e.g., where the lid is unscrewed from the vial and lifted upwards to remove the injector from the container containing corneal storage medium). The tubing of the coupling device can also be removed along with the injector from the remainder of the injector carrier, where the tubing, still attached to the injector, can be coupled to a syringe or other device for dispensing the ophthalmic tissue from the injector during endothelial keratoplasty, for example. The tubing can also be flexible to universally accommodate the coupling of syringes of various dimensions and configurations.

EXAMPLES

Example embodiments of the present technology are provided with reference to the several figures enclosed herewith.

With reference to FIGS. 1-2, an embodiment of a needle injector 100 is shown having a first portion 105, a second portion 110, and a third portion 115. The first portion 105 includes a first conduit 120 having a first end 125 and a second end 130. The second portion 110 includes a second conduit 135 having a first end 140 and a second end 145. The first end 140 of the second conduit 135 is fluidly coupled to the second end 130 of the first conduit 120, where in the embodiment of the needle injector 100 depicted, the first portion 105 and the second portion 110 are formed of a single piece of material. The second conduit 135 has a maximum diameter 150 greater than a maximum diameter 155 of the first conduit 120. The third portion 115 does not include any openings along its length but does include a third conduit 160 having a first opening at a first end 165 and a second opening at a second end 170 where the first opening and the second opening are the only structures of the third portion through which fluid can pass. The first end 165 of the third conduit 160 is configured to be fluidly coupled to the second end 145 of the second conduit 135. The second end 170 of the third conduit 160 is configured with a cutting surface 175 for cutting and penetrating eye tissue.

In the needle injector 100 depicted, the first end 165 of the third conduit 160 can be reversibly fluidly coupled to the second end 145 of the second conduit 135, where FIG. 1 shows the coupled state and FIG. 2 shows the uncoupled state. The first conduit 120 and the second conduit 135 are comprised by a single piece of glass and the cutting surface 175 at the second end 170 of the third conduit 160 is comprised by metal. The cutting surface 175 is located at a distal end of an opening 180 at the second end 170 of the third conduit 160 and a remainder of the opening 180 has a non-cutting surface 185. A bulb 190 is disposed between the first end 125 and the second end 130 of the first conduit 120. As shown, at least a portion of the second conduit 135 tapers in a direction from the first end 140 of the second conduit 135 towards the second end 145 of the second conduit 135. The second end 145 of the second conduit 135 has a diameter 195 that is less than the maximum diameter 155 of the first conduit 120. The second end 145 of the second conduit 135 is also configured to fit into the first end 165 of the third conduit 160.

Figure 6:
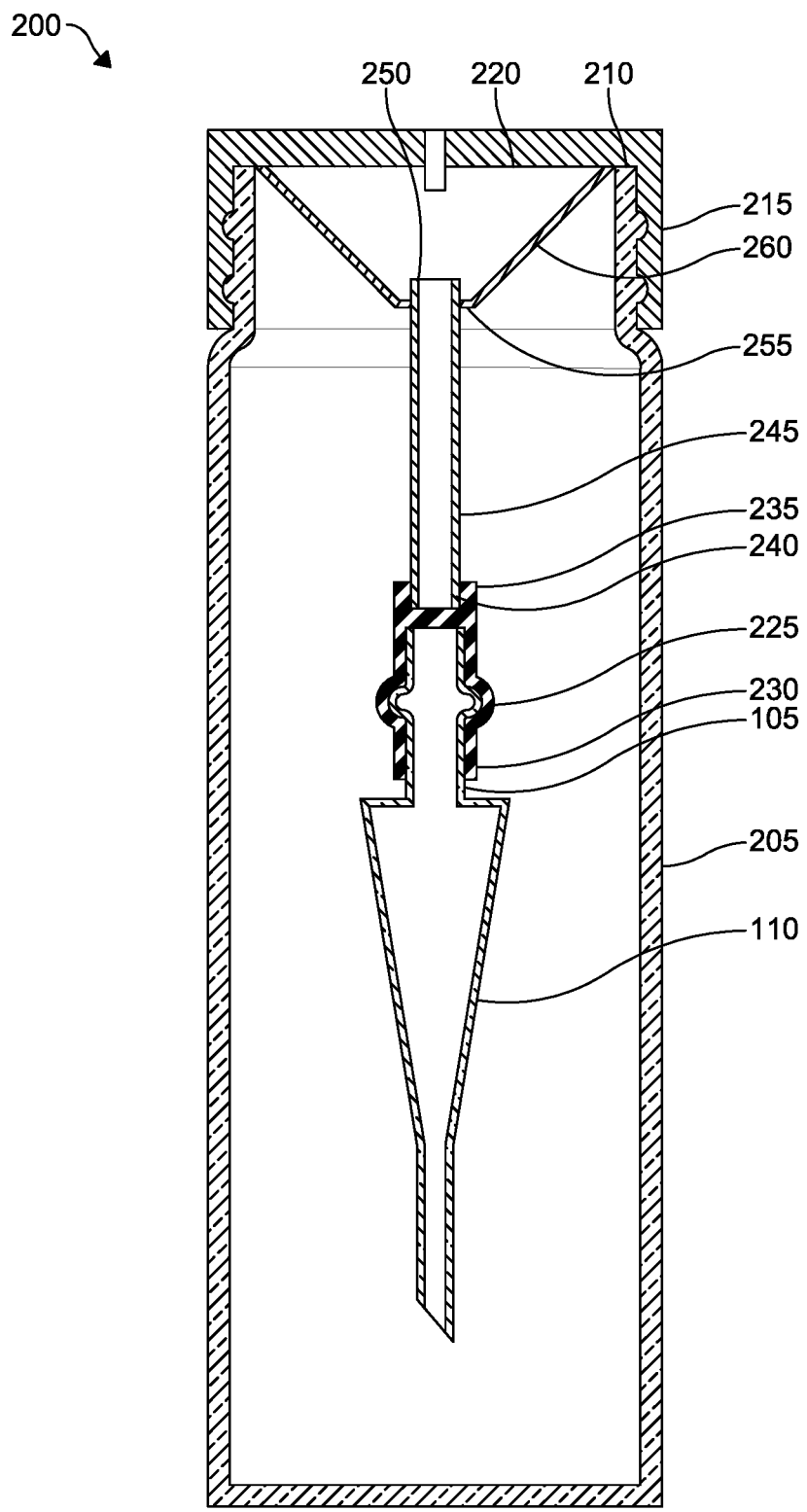
FIG. 6 shows cross-sectional assembled view of the embodiment of a carrier for a needle injector according to FIG. 3.

With reference to FIGS. 3-6, an embodiment of an injector carrier 200 is shown in conjunction with the first and second portions 105, 110 of the needle injector 100 of FIGS. 1-2. It should be recognized that while the injector carrier 200 in use with the needle injector 100 of FIGS. 1-2, the injector carrier 200 can be used with other injectors or introducers used in the art for dispensing ophthalmic tissue in an endothelial keratoplasty procedure. It should be further recognized that injector carrier 200 can be configured to accommodate just the first and second portions 105, 110 of the needle injector 100 as shown (e.g., the third portion is uncoupled from the second portion) or where the third portion 115 is coupled to the second portion 110. Where the injector carrier 200 is used in conjunction with just the first and second portions 105, 110 of the needle injector 100, the third portion 115 can be provided or packaged separately; e.g., packaged similarly to a sterile hypodermic needle. The embodiment of the injector carrier 200 depicted includes a container 205 having an opening 210, a cap 215 configured to seal the opening 210 of the container 205, and a coupling means 220 configured to couple the first portion 105 of the needle injector 100 to the cap 215 and allow at least the first portion 105 and the second portion 110 of the needle injector 100 to be disposed within the container 205 when the cap 215 seals the opening 210 of the container 205. As shown in FIGS. 3 and 6, at least the first and second portions 105, 110 of the needle injector 100 can be disposed within the container 205 without contacting the container 205.

In the embodiment shown, the coupling means 220 of the injector carrier 200 includes a resilient member 225 having a first end 230 configured to fit over the first end 125 of the first conduit 120 of the needle injector 100. The resilient member 225 also has a second end 235 that fits over a first end 240 of a stem 245 coupled to the cap 215. The second end 250 of the stem 245 is fit into an opening 255 within a sealing member 260 coupled to the cap 215, where the sealing member 260 is configured to seal the opening 210 of the container 205. As shown, the sealing member 250 is has a frustoconical shape where the larger end engages the cap 215 and the smaller end has the opening 255 that receives the second end 250 of the stem 245.

Figure 7:
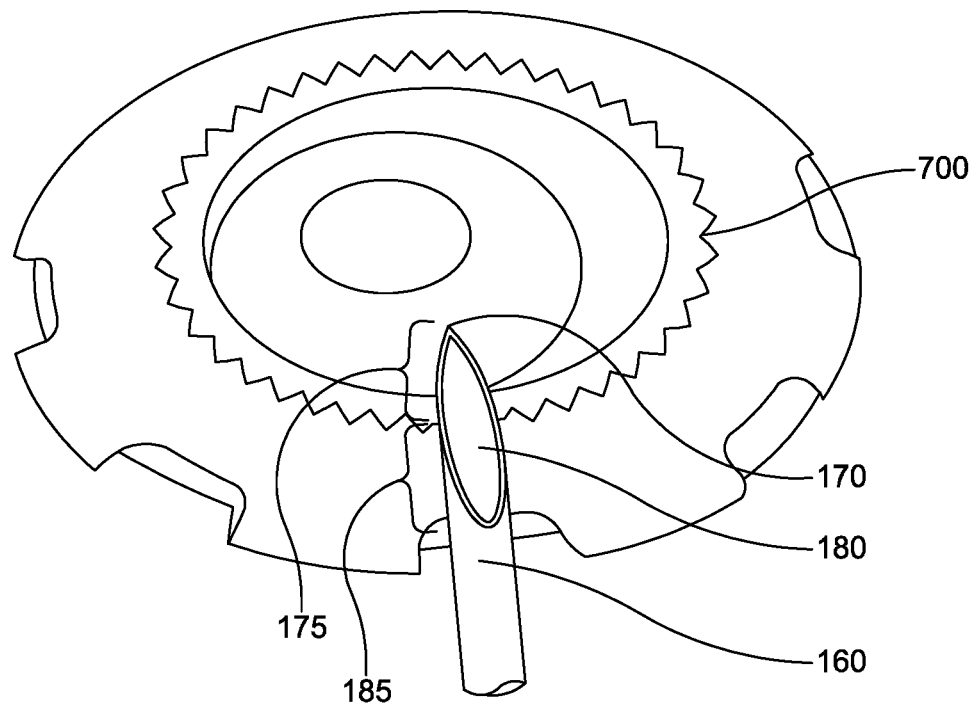
FIG. 7 shows a needle portion of a needle injector being introduced into an eye for delivery of a graft.
Figure 8:
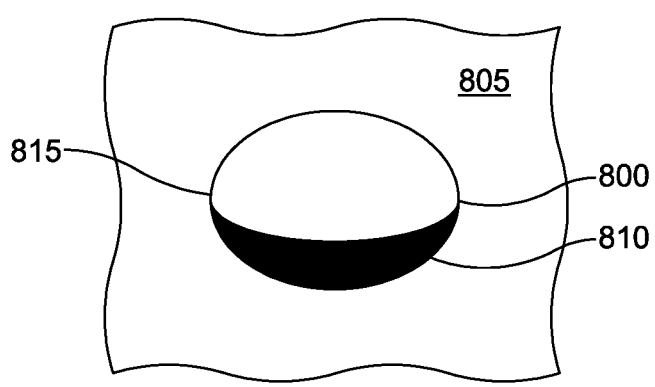
FIG. 8 shows the wound profile of the needle injector of FIG. 7.

The following examples were used to evaluate endothelial cell viability of prepared DMEK grafts of ophthalmic tissue in conjunction with use of the needle injector 100. All grafts of ophthalmic tissue were pre-loaded into a needle injector 100 for use in DMEK and PDEK and then the ophthalmic tissue was injected into an artificial anterior chamber, replicating the anterior chamber of the human eye, as follows. Three (n=3) DMEK grafts were prepared using a no-touch hydrodissection method and stained with Trypan Blue, then trephined with an 8 mm donor punch. Each graft was loaded into a needle injector 100, stored for 1 day in Optisol-GS at 2-8° C., and then injected into the artificial anterior chamber replicating the anterior chamber of the human eye. FIG. 7 depicts insertion of the second end 170 of the third conduit 160 into the artificial anterior chamber 700, wherein the cutting surface 175 cuts and penetrates into the artificial anterior chamber 700. The ophthalmic tissue is then dispensed from the second conduit 135 of the needle injector 100 through the third conduit 160 of the needle injector 100 into the artificial anterior chamber 700. A close-up of an insertion profile 800 into the outer surface 805 of the artificial anterior chamber 700 is shown in FIG. 8, where a cut 810 is made by the cutting surface 175 and a mark 815 is visible where the non-cutting surface 185 pushes through into the artificial anterior chamber 700, but does not cut the outer surface 805, as the entire opening 180 at the second end 170 of the third conduit 160 is inserted into the artificial anterior chamber 700. As can be seen from the insertion profile 800, the actual cut 810 into the outer surface 805 of the artificial anterior chamber 700 is less than the outer diameter of the third conduit 160 (e.g., a cut of about 1.3 mm for a 1.6 mm outer diameter) which minimizes trauma to the eye tissue and improves healing. For example, the non-cutting surface 185 of the beveled opening 180 can push through the cut 810 without further cutting and increasing the size of the cut 810 in the outer surface 805 of the artificial anterior chamber 700.

Viability of the corneal endothelium introduced into the artificial anterior chamber 700 was evaluated by slit lamp, specular microscopy, and cell staining, where cells were stained with Trypan Blue (0.4%), processed, and analyzed using "ImageJ" software to quantitate the stained portion. In the needle injector 100, the prepared graft of ophthalmic tissue moves in one direction; e.g., the graft is loaded from the wider end at the first end 125 of the first conduit 120 (e.g., about 2 mm inner diameter) in order to reduce the potential for endothelial damage. The graft of ophthalmic tissue then is dispensed and unloads from the narrow end of glass tube (e.g., first and second portions 105, 110), through the second end 145 of the second conduit 135, which is inside the first end 165 of the third conduit 160 (e.g., the needle). The first end 165 of the third conduit 160 is placed over the narrow second end 145 of the second conduit 135, where the second end 145 of the second conduit 135 can be positioned at the beginning of the beveled opening 180 of the third conduit 160 to reduce exposure of the ophthalmic tissue to the metal of the third conduit 160. In this configuration, contact between the endothelium and metal inner surface of the third conduit 160 is minimized or even eliminated.

Endothelial cell density was evaluated as follows. Prior to DMEK tissue preparation, mean endothelial cells density was determined to be about 2434 cells/mm$^2$. After the graft of ophthalmic tissue for DMEK was prepared, mean endothelial cell density was determined to be about 2634 cells/mm$^2$. After dispensing through the needle injector 100 into the artificial anterior chamber 700, mean endothelial cell density was determined to be about 2486 cells/mm$^2$. Endothelial cell staining evaluation confirmed viable endothelium with only about a 3% increase of damaged cells (e.g., from 1.5% to 4.5%). Thus, the present needle injector 100 can be used to provide efficient dispensing of ophthalmic tissue into an eye while minimizing damage to the introduced graft.

The following example, compares the wound architecture as illustrated by the insertion profile 800 of the needle injector 100 with the wound architecture resulting from use of a glass injector as used in other methods of performing endothelial keratoplasty. The outside diameter of the third conduit 160 (e.g., the metal needle) of the needle injector 100 used was 1.6 mm and the outside diameter of the dispensing end of the glass injector was 1.6 mm. As such, the needle injector 100 and the glass injector as used in other methods of performing endothelial keratoplasty each required the same sized diameter to be inserted into the eye. As shown in FIG. 8, the needle injector 100 results in an insertion profile 800 where the actual cut 810 into the outer surface 805 of the artificial anterior chamber 700 is less than the outer diameter of the third conduit 160; e.g., a cut of about 1.3 mm for a 1.6 mm outer diameter.

Figure 9:
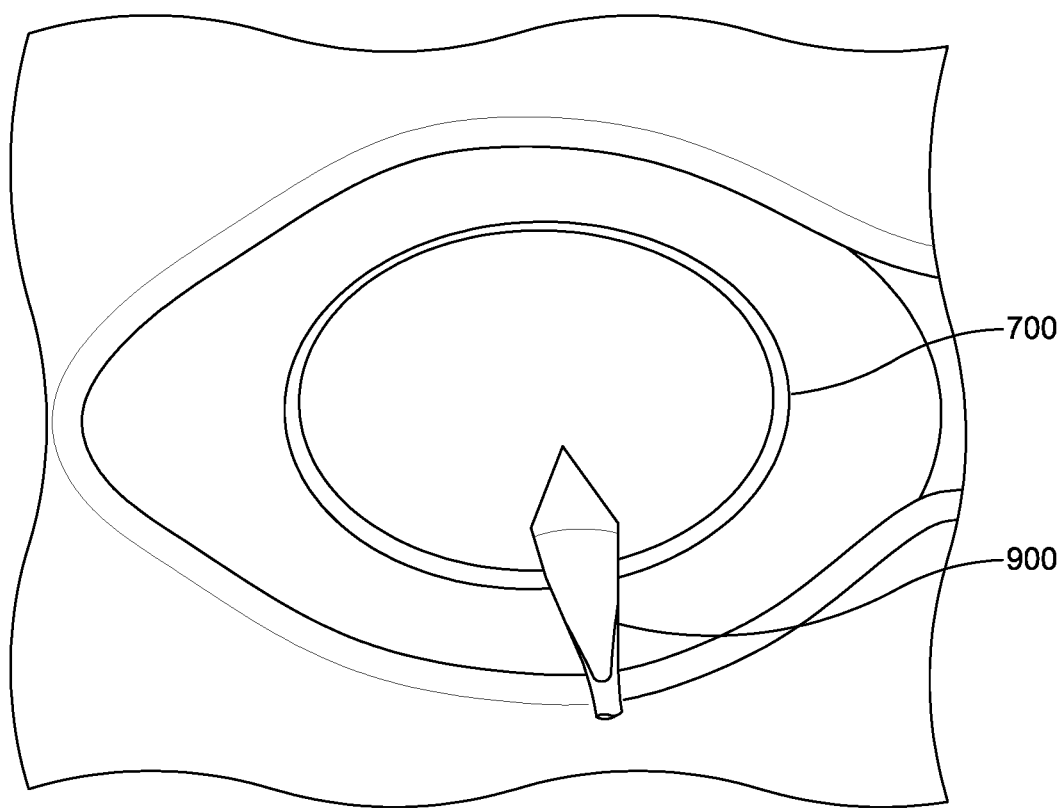
FIG. 9 shows a scalpel making an incision in an eye so that an injector or introducer without a needle portion can introduce a graft through the incision.
Figure 10:
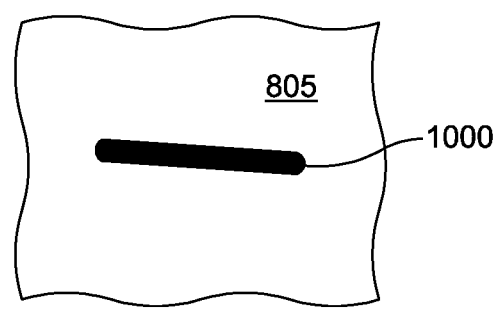
FIG. 10 shows the wound profile of the scalpel of FIG. 9.

Insertion of the end of the glass injector used in other methods of performing endothelial keratoplasty, however, requires that an incision be first made with a scalpel 900, as shown in FIG. 9. The scalpel 900 is removed and the dispensing end of the glass injector is then inserted into the artificial anterior chamber 700. This results in the insertion profile 1000 shown in FIG. 10. The insertion profile 1000 in this instance is equal to the actual cut into the outer surface 805 of the artificial anterior chamber 700, which is greater than the diameter of the dispensing end of the glass injector. In particular, it is not possible to insert the glass injector through a 1.6 mm incision, even though the dispensing end of the glass injector has a 1.6 mm diameter. Fully inserting the glass injector requires a minimum incision size of 2.2 mm. When a 2.2 mm blade of the scalpel 900 enters into tissue, a 2.2 mm straight wound is formed, as shown in FIG. 10.

Multiple measurements have identified that use of a glass injector requires about a 0.6 mm incremental wound size than the present needle injector 100, where the needle injector results in a cut 810 of about 1.6 mm versus the the glass injector incision size of about 2.2 mm. Other types of glass injectors and introducers used in the art can even require incisions from about 2.6 mm to about 3.6 mm. Accordingly, the different wound architecture of using the needle injector 100 and the smaller incision/cut formed in the eye surface serve to minimize trauma and improve healing of the eye. Likewise, wound architecture of the crescent shape of the insertion profile 800 from the needle injector 100 versus a blade incision promotes sutureless wound healing. These aspects can combine to be less invasive and result in smaller wounds, where the ability to forgo the use of a suture can further reduce potential for astigmatism. Thus, the present needle injector 100 has demonstrated certain benefits and advantages over glass injectors or introducers that require a scalpel incision for their use.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A needle injector for endothelial keratoplasty in combination with an injector carrier comprising:
    (a) a first portion comprising a first conduit having a first end, a second end, and a first conduit maximum diameter;
    (b) a second portion comprising a second conduit having a first end, a second end, and a second conduit maximum diameter, wherein
        (i) the maximum diameter of the second conduit second end is less than the first conduit maximum diameter, and wherein
        (ii) the first end of the second conduit is fluidly coupled to the second end of the first conduit, and
        (iii) the second conduit defines a chamber having an interior diameter and a chamber length that are sized to store an endothelium tissue layer coupled to a Descemet membrane and sized to provide corneal storage media irrigation to the ophthalmic tissue graft; and
    (c) a third portion comprising a third conduit having a first end with a first opening and a second end, and a third portion length that extends along a straight line from the first end to the second end such that the third portion is not curved, wherein
        (i) the first end of the third conduit is fluidly coupled to the second end of the second conduit, and wherein
        (ii) the second end of the third conduit comprises a second opening configured to dispense an endothelium tissue layer coupled to a Descemet membrane, and wherein
        (iii) the third portion does not comprise any openings along the length, and wherein
        (iv) the first opening and the second opening are the only structures of the third portion through which fluid can pass; and
    (d) an injector carrier, the injector carrier comprising
        (i) a container having an opening,
        (ii) cap configured to seal the opening of the container, and
        (iii) at least the first portion and the second portion disposed within the container.

2. The needle injector according to claim 1, wherein:
    (a) the second end of the third conduit comprises a beveled opening having a leading portion and a trailing portion; and wherein
    (b) the leading portion comprises (i) a cutting surface for cutting and penetrating eye tissue, and (ii) the trailing portion comprises a non-cutting surface.

3. The needle injector according to claim 1, wherein the first conduit and the second conduit are comprised by a single piece of glass.

4. The needle injector according to claim 2, wherein the cutting surface is comprised by metal.

5. The needle injector according to claim 1, wherein:
(a) the second portion comprises (i) a first position located a first distance from the first end, and (ii) a second position that has a smaller cross-sectional diameter than the first position and that located a second distance from the first end;
(b) the second distance is greater than the first distance; and wherein
(c) the second portion tapers from the first position to the second position.

6. The needle injector according to claim 1, wherein the first conduit has a bulb disposed between the first end and the second end thereof.

7. The needle injector according to claim 1, further comprising a coupling means configured to couple the first portion of the needle injector to the cap and allow at least the first portion and the second portion of the needle injector to be disposed within the container when the cap seals the opening of the container.

8. The needle injector according to claim 7, wherein
(a) the coupling means comprises a resilient member having (i) a first end configured to fit over the first end of the first conduit, and (ii) a second end that fits over a first end of a stem coupled to the cap; and wherein
(b) the coupling means is configured to couple the first portion of the needle injector to the cap and allow at least the first portion and the second portion of the needle injector to be disposed within the container when the cap seals the opening of the container without contacting the container.

9. The needle injector according to claim 8, wherein a second end of the stem is fit into an opening within a sealing member coupled to the cap, the sealing member configured to seal the opening of the container.

10. The needle injector according to claim 7, wherein the container includes corneal storage medium.

11. The needle injector according to claim 1, wherein the container includes corneal storage medium.

12. The needle injector according to claim 11, wherein (i) the chamber includes an ophthalmic tissue graft, and (ii) the ophthalmic tissue graft contacts the corneal storage medium.

13. A method for performing endothelial keratoplasty for an eye of a patient comprising:
(a) providing a needle injector comprising
(i) a first portion comprising a first conduit having a first end, a second end, and a first conduit maximum diameter,
(ii) a second portion comprising a second conduit comprising (A) a first end, (B) a second end having a second conduit end maximum diameter, (C) a second portion length that extends between the first end of the second conduit and the second end of the second conduit, wherein
the first end of the second conduit is fluidly coupled to the second end of the first conduit,
the second conduit end maximum diameter is less than the first conduit maximum diameter,
the second conduit defines a chamber, wherein (I) the chamber extends at least partially along the second portion length, (II) the chamber tapers from a wider end to a narrower end, wherein the wider end is closer to the first portion than the narrower end, and (III) the chamber has an interior diameter and a chamber length that are sized to store an ophthalmic tissue graft and sized to provide corneal storage media irrigation to the ophthalmic tissue graft; and
(iii) a third portion comprising (A) a third conduit having a first end with a first opening and a second end with a second opening, and further comprising (B) a third portion length that extends along a straight line from the first end to the second end such that the third portion is not curved, wherein
the first end of the third conduit is fluidly coupled to the second end of the second conduit,
the second end of the third conduit comprises an opening having a beveled surface that is structured to penetrate eye tissue to dispense an endothelium tissue layer coupled to a Descemet membrane,
wherein the endothelium tissue layer coupled to the Descemet membrane is positioned within the chamber,
the third portion does not comprise any openings along the length, and
the third conduit first opening and second opening are the only structures of the third portion through which fluid can pass;
(b) inserting the second end of the third conduit into the eye of the patient, wherein the second end of the third conduit penetrates the eye of the patient; and
(c) dispensing the endothelium tissue layer coupled to the Descemet membrane from the chamber of the needle injector through the third conduit of the needle injector into the eye of the patient.

14. A method of storing ophthalmic tissue for use in endothelial keratoplasty comprising:
(a) providing a needle injector comprising
(i) a first portion comprising a first conduit having a first end, a second end, and a first conduit maximum diameter;
(ii) second portion comprising a second conduit having a first end, a second end, and a second conduit maximum diameter, wherein
the maximum diameter of the second conduit second end is less than the first conduit maximum diameter, and wherein
the first end of the second conduit is fluidly coupled to the second end of the first conduit, and
the second conduit defines a chamber having an interior diameter and a chamber length that are sized to store an endothelium tissue layer coupled to a Descemet membrane and sized to provide corneal storage media irrigation to the ophthalmic tissue graft; and
(iii) a third portion comprising a third conduit having a first end with a first opening and a second end, and a third portion length that extends along a straight line from the first end to the second end such that the third portion is not curved, wherein
the first end of the third conduit is fluidly coupled to the second end of the second conduit, and wherein
the second end of the third conduit comprises a second opening configured to dispense an endothelium tissue layer coupled to a Descemet membrane, and wherein
the third portion does not comprise any openings along the length, and wherein the first opening and the second opening are the only structures of the third portion through which fluid can pass,
(iv) an injector carrier, the injector carrier comprising
a container having an opening, wherein the container includes corneal storage medium,
cap configured to seal the opening of the container, and
at least the first portion and the second portion disposed within the container;
(b) loading the chamber with an endothelium tissue graft coupled to the Descemet membrane so that the endothelium tissue graft coupled to the Descemet membrane contacts the corneal storage medium; and
(c) transporting the injector carrier including the loaded chamber to a site for performing endothelial keratoplasty.

\* \* \* \* \*